United States Patent [19]

Moormann et al.

[11] Patent Number: 4,523,020

[45] Date of Patent: Jun. 11, 1985

[54] SUBSTITUTED 2-(3-AMINOPHENOXYMETHYL)IMIDAZO-LINES

[75] Inventors: Alan E. Moormann; Barnett S. Pitzele, both of Skokie; Peter H. Jones, Lake Bluff, all of Ill.

[73] Assignee: G. D. Searle & Co., Skokie, Ill.

[21] Appl. No.: 550,334

[22] Filed: Nov. 10, 1983

[51] Int. Cl.$^3$ .......................................... C07D 233/22
[52] U.S. Cl. .................................. 548/353; 549/313; 560/23; 560/45
[58] Field of Search ........................................ 548/353

[56] References Cited

U.S. PATENT DOCUMENTS

| 3,449,356 | 6/1969 | White | 548/353 |
| 3,449,357 | 6/1969 | White | 548/353 |
| 3,966,757 | 6/1976 | Baganz et al. | 548/353 |
| 4,025,639 | 5/1977 | Baganz et al. | 424/273 R |
| 4,163,105 | 7/1979 | Wysong | 548/353 |
| 4,226,876 | 10/1980 | Copp et al. | 548/353 X |

FOREIGN PATENT DOCUMENTS

| 76/1508 | 3/1976 | South Africa | 548/353 |
| 78/2449 | 4/1978 | South Africa | 548/353 |

*Primary Examiner*—Richard A. Schwartz
*Attorney, Agent, or Firm*—John J. McDonnell

[57] ABSTRACT

This invention relates to novel substituted 2-(3-aminophenoxymethyl)imidazolines which are useful for the treatment of diarrhea and useful as analgesics.

13 Claims, No Drawings

SUBSTITUTED 2-(3-AMINOPHENOXYMETHYL)IMIDAZOLINES

BACKGROUND OF THE INVENTION (a) Field of the Invention

This invention relates to novel substituted 2-(3-aminophenoxymethyl)imidazolines of Formula I principally useful in the treatment of diarrhea and also useful as analgesics.

Diarrhea is a condition characterized by an abnormally frequent discharge of liquid or semi-liquid from the bowel. The normal intestinal discharge occurs at variable intervals but usually not more than twice in twenty-four hours and typically has a semi-solid consistency. When a more liquid stool must be discharged more than three times a day, diarrhea exists. Diarrhea may have any of several causes. For example, eating indigestible or irritating foods or foods to which an individual is allergic may cause diarrhea. Too much roughage, such as found in bran, cabbage, or other fibrous foods often consumed to relieve constipation, may also induce diarrhea. Infection or nervousness, which can cause discharge before the intestinal contents can assume a normal form, are causes of diarrhea. Moreover, many drugs, particularly antibiotics, are known to cause diarrhea as a side effect.

Mild diarrhea has been treated with binding agents such as aluminum hydroxide gel, kaolin, pectin, and bismuth. More serious diarrhea has been treated with opiates, which act through a spasmogenic effect that inhibits propulsive activity in the intestine. Diphenoxylate (a synthetic opiate derivative), tincture of opium, and camphorated tincture of opium (paregoric) have all been used effectively for serious diarrhea. The compounds, however, treat symptoms rather than causes and have all the problems associated with opiates, such as addictive liability, mental confusion or discomfort, respiratory depression, nausea, and the like. Thus, care must be taken to avoid complications and even death.

Analgesics are agents used in the treatment of pain and often are useful in alleviating inflammation. The major classes of analgesics include narcotic analgesics (or opiates) and analgesic-antipyretics such as the salicylates. Although the efficacy of opiates in relieving pain is well-established, the associated addiction liability is a distinct disadvantage. Although salicylate and salicylate-like agents are also efficacious in relieving pain, they often exhibit undesirable side effects such as gastrointestinal irritation (as with aspirin) or liver toxicity with extended use (as with acetaminophen). The compounds included in this invention are neither opiates nor salicylates and may be expected not to exhibit the disadvantages of either class of compound.

(b) Prior Art

Certain substituted 2-(phenoxymethyl)imidazolines are known—U.S. Pat. Nos. 3,966,757 and 4,025,639 (both to A. Nattermann & Cie. GmbH.), and South African patent application Nos. 76/1508 (Takeda Chemical Industries Ltd.) and 78/2449 (Ciba-Geigy A.G.)—but differ significantly from the present compounds. In the previously disclosed compounds, the phenyl nucleus bears only hydrogen, alkyl, alkoxy, nitro, or halogen substituents, but never bears amino or substituted-amino groups as disclosed here for the first time. Moreover, the prior art compounds were disclosed as hypotensives U.S. Pat. Nos. 3,966,757 and 4,025,639 and as parasiticides (76/1508 and 78/2449).

SUMMARY OF THE INVENTION

The following compounds have been discovered to be useful as antidiarrheals which act by decreasing aqueous secretion in the intestines. Since the compounds do not exhibit the problems associated with opiates and since they act at the source of the condition rather than on the symptoms, the associated complications inherent in optiates may be eliminated. These compounds have also been discovered to be useful as analgesic agents.

The invention relates to compounds of Formula I:

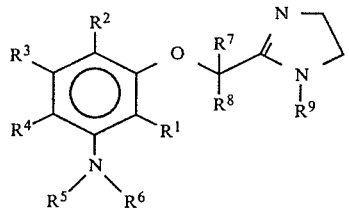

wherein $R^1$ and $R^3$, each being the same or different, are:
  (a) hydrogen; or
  (b) alkyl of 1 to 6 carbon atoms, inclusive;
wherein $R^2$ and $R^4$, each being the same or different, are:
  (a) hydrogen;
  (b) alkyl of 1 to 6 carbon atoms, inclusive; or
  (c) halogen; with the proviso that $R^1$ and $R^2$ may not both be hydrogen;
wherein $R^5$ is:
  (a) hydrogen; or
  (b) alkyl of 1 to 6 carbon atoms, inclusive;
wherein $R^6$ is:
  (a) hydrogen;
  (b) alkyl of 1 to 6 carbon atoms, inclusive;
  (c) alkanoyl of 2 to 7 carbon atoms, inclusive; or
  (d) alkoxycarbonyl of 2 to 7 carbon atoms, inclusive;
wherein $R^7$ is:
  (a) hydrogen; or
  (b) alkyl of 1 to 6 carbon atoms, inclusive;
wherein $R^8$ is:
  (a) alkyl of 1 to 6 carbon atoms, inclusive; or
  (b) $(CH_2)_nOR^{10}$;
wherein $R^9$ is:
  (a) hydrogen; or
  (b) alkyl of 1 to 6 carbon atoms, inclusive;
wherein $R^{10}$ is:
  (a) hydrogen; or
  (b) alkanoyl of 2 to 7 carbon atoms, inclusive;
wherein n is an integer of 1 to 6, inclusive; and the pharmacologically acceptable salts; the compounds being either hydrated or unhydrated.

Examples of alkyl of 1 to 6 carbon atoms, inclusive, are methyl, ethyl, propyl, butyl, pentyl, hexyl, and the isomeric forms thereof, generally referred to as alkyl.

Examples of alkanoyl of 2 to 7 carbon atoms, inclusive, are acetyl, propanoyl, butanoyl, pentanoyl, hexanoyl, and the isomeric forms thereof.

Examples of alkoxycarbonyl of 2 to 7 carbon atoms, inclusive, are methoxycarbonyl, ethoxycarbonyl, propoxycarbonyl, butoxycarbonyl, pentoxycarbonyl, hexoxycarbonyl, and the isomeric forms thereof.

Examples of halogen are fluorine, chlorine, bromine, and iodine.

Examples of pharmacologically acceptable acid addition salts include the hydrochloride, hydrobromide, hydroiodide, sulfate, phosphate, acetate, propionate, lactate, maleate, malate, succinate, and tartrate salts.

DESCRIPTION OF THE INVENTION

The compounds of this invention are prepared by the following general methods. A preferred general method is illustrated in Scheme A.

Scheme A

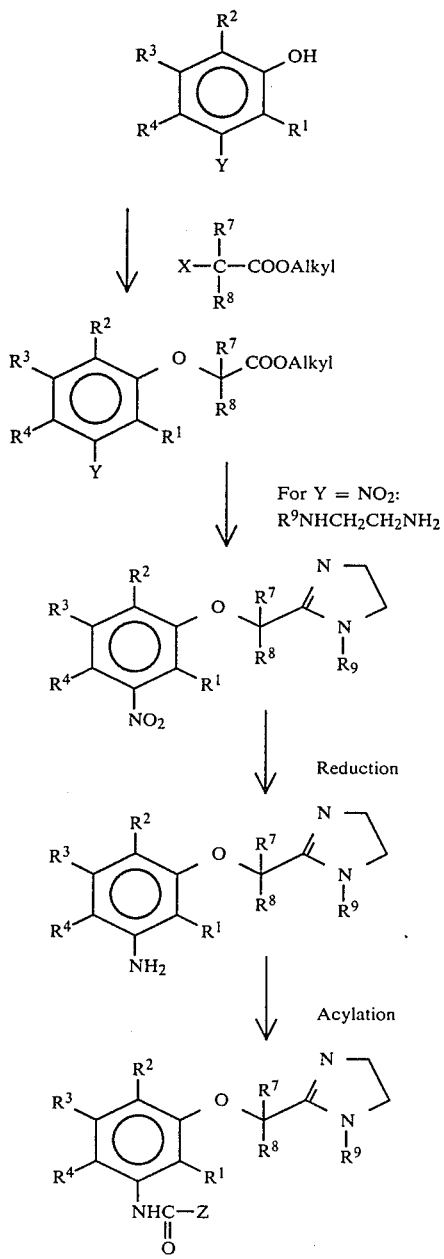

Substituted phenols of Formula II react with 2-haloalkanoate esters of Formula III to form 2-phenoxyalkanoates of Formula IV. Typically the reactions are performed in relatively unreactive organic solvents containing an inorganic or hindered organic base. In a preferred method, an alkyl 2-bromoalkanoate is stirred in dimethylformamide containing an inorganic base, such as sodium or potassium carbonate. Where the phenols of Formula II are 3-nitrophenols (i.e., where Y is $NO_2$), the subsequently formed 2-(3-nitrophenoxy)alkanoates of Formula IV need no further modification before conversion to intermediates of Formula V. Where, however, the phenols of Formula II are not already nitro derivatives (i.e., where Y is hydrogen), the subsequently formed intermediates IV must be nitrated to give the corresponding 2-(3-nitrophenoxy)alkanoates. Nitration conditions include addition of nitric acid to a solution of compounds IV in cold (less than 0°) sulfuric acid. Typically, 3-nitro derivatives must be separated from other nitrated by-products by crystallization or column chromatography.

Imidazolines of Formula V are subsequently formed from the esters, Formula IV, by reaction with 1,2-diaminoethane (or an N-alkylated diaminoethane) which has been activated with trialkylaluminum. Typically the diamine and trimethylaluminum are mixed in a cold (below about 0°) organic solvent and the adduct then heated with the ester, Formula IV. Preferably, the reaction is performed in toluene, which is heated at reflux for the second part of the cyclization procedure. An alternative, but less favored, cyclization to the imidazolines (especially where N-alkylated) employs acid-catalyzed dehydration at elevated temperatures. In a preferred set of conditions, an anhydrous mixture of an ester of Formula IV, the appropriate diamine, and a non-volatile acid (such as p-toluenesulfonic acid) is heated without solvent to about 230°–270°.

Reduction of the intermediate nitro intermediates, Formula V, affords the amino compounds of this invention, Formula VI. Typically the reduction involves catalytic hydrogenation in an acidic medium. Preferred conditions include hydrogenation in ethanol containing hydrochloric acid and using 10% palladium on carbon as catalyst. The amines thus formed are isolated as dihydrochloride salts. Under these conditions compounds of Formula V bearing halogen substitution (typically bromine) on the phenyl ring are generally dehalogenated and thus form the corresponding hydrogen-substituted compound. An alternative milder method of reduction may be selected in order to lessen the dehalogenation. For example, a preferred method utilizes Raney nickel instead of hydrogenation over palladium.

Acylated derivatives of Formula VII, in which typical acyl groups include alkanoyl (where Z is alkyl of 1 to 6 carbon atoms, inclusive) or alkoxycarbonyl (where Z is alkoxy of 1 to 6 carbon atoms, inclusive), may be prepared by any of several methods known to those skilled in the art. In any event, acylation at an imidazoline nitrogen is suppressed by using the acid addition salts of compounds VI (the preferred method) or by employing acidic reaction conditions. Alkanoyl derivatives may be prepared by reaction of amines of formula VI with an alkanoyl halide, such as acetyl chloride and the like, or an alkanoic anhydride, such as acetic anhydride and the like, in an organic solvent. Preferred conditions for preparing acetyl derivatives, for example, include reaction of compounds VI with acetic anhydride in acetonitrile at room temperature. Alkoxycarbonyl derivatives may be prepared by reaction of amines of Formula VI with an alkoxycarbonyl halide, such as ethyl chloroformate and the like, or a dialkyl dicarbonate, such as diethyl pyrocarbonate and the like, in an organic solvent. Alternatively, alkoxycarbonyl derivatives may be prepared by reaction of the amine with phosgene in an unreactive organic solvent, followed by addition of the appropriate alkanol. Preferred conditions include initial reaction of compounds VI with phosgene in acetonitrile, followed by reaction of an alcohol such as anhydrous ethanol.

Scheme B, a partial modification of the above procedure, is preferred for preparing the compounds of this invention, Formula I, where $R^8$ is hydroxyalkyl.

Scheme B

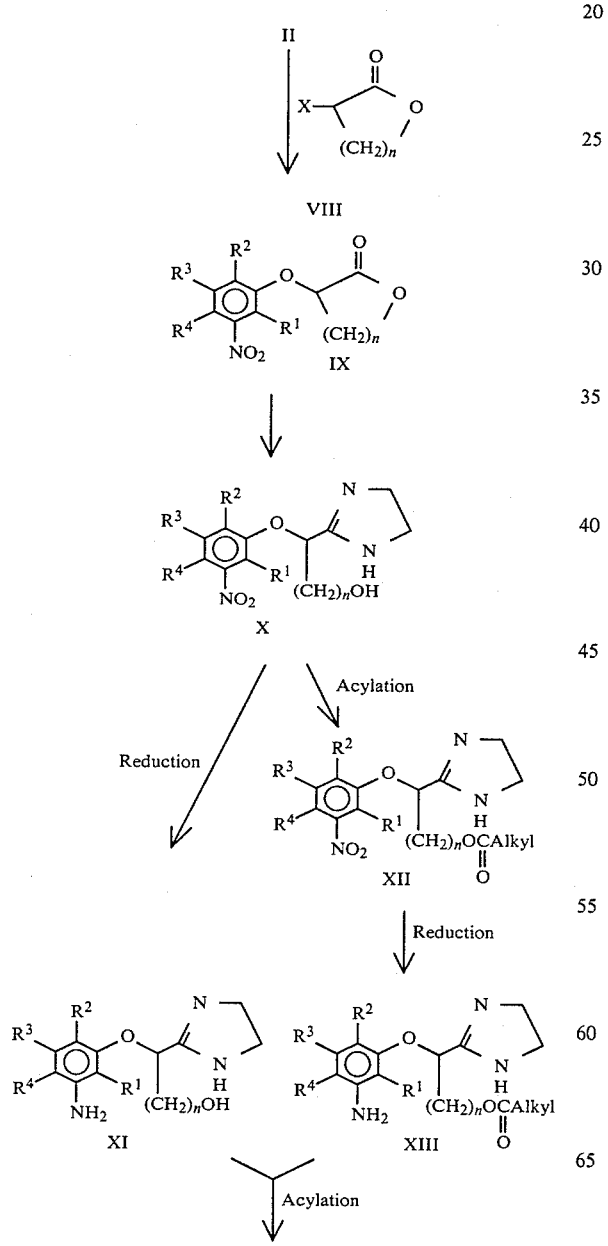

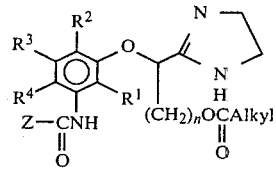

Thus, under the same conditions described above (See Scheme A), 2-bromo gamma-lactones, Formula VIII, react with 3-nitrophenols of Formula II ($Y=NO_2$) to form intermediates of Formula IX. As before, reaction of lactones IX with diamines forms imidazoline compounds, but concomitant opening of the lactone ring also exposes a hydroxyl group, thus forming compounds of Formula X. Subsequent reduction of the nitro function by the methods described above (See Scheme A) affords amino compounds of this invention, Formula XI. Alternatively, the nitro compounds, Formula X, may be acylated by any of several methods known to the art to produce derivatives of Formula XII. Subsequent reduction of the nitro group then affords amino compounds of this invention, Formula XIII. Moreover, the amino groups of compounds of either Formula XI or Formula XIII may be acylated as described above in Scheme A to give multiply acylated compounds, Formula XIV.

Scheme C illustrates a method for preparing compounds of this invention where the amino group is N-alkylated.

Scheme C

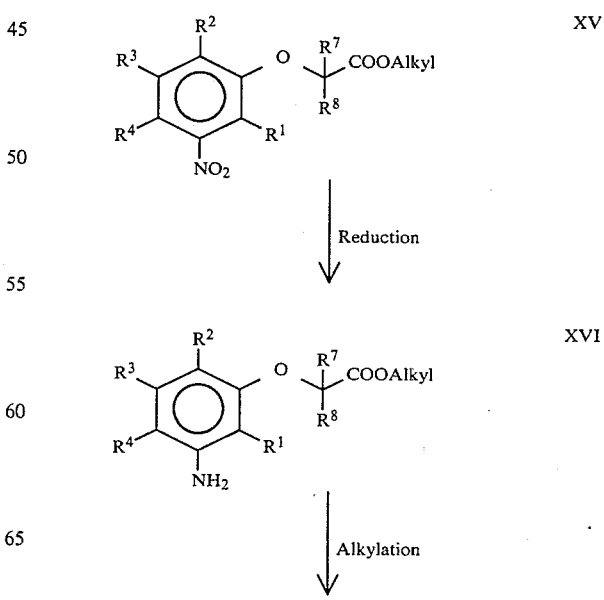

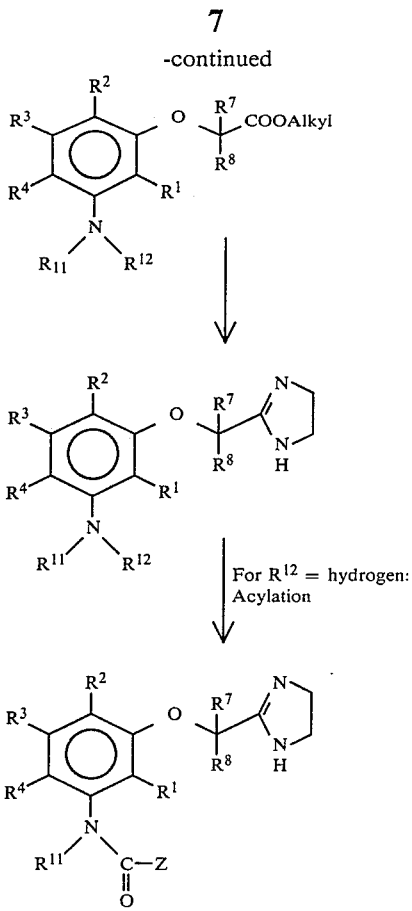

XVII

XVIII

For R¹² = hydrogen: Acylation

XIX

Reduction of the nitro group of 2-(3-nitrophenoxy)alkanoates of Formula XV affords corresponding 2-(3-aminophenoxy)alkanoates of Formula XVI. (Reactions using lactones of Formula IX would proceed analogously.) Intermediates of Formula XVII may then be prepared by N-alkylation using methods known to the art. For example, compounds XVI can react with alkyl halides or sulfates to form monoalkyl or dialkyl derivatives. Other methods may also be employed. A preferred method for preparing N,N-dimethyl derivatives employs a mixture of 37% formaldehyde and sodium borohydride in acetonitrile containing acetic acid. Subsequent cyclization to the imidazolines, using methods described above (See Scheme A), affords N-alkylated compounds of this invention, Formula XVIII. Acylation of N-monoalkylated members of this series using methods described above (See Scheme B) affords compounds of this invention, Formula XIX.

The preferred embodiments of this invention include compounds of the following general structure, Formula XX.

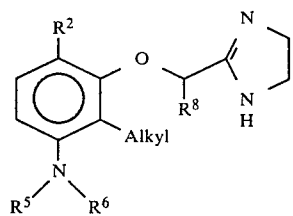

XX

More specifically, the preferred embodiments include compounds of Formula XX wherein $R^2$ is hydrogen or lower alkyl (that is, consisting of 1 to 6 carbon atoms, inclusive); wherein $R^5$ and $R^6$ are hydrogen, lower alkyl, lower alkanoyl (that is, consisting of 2 to 7 carbon atoms, inclusive), or lower alkoxycarbonyl (that is, consisting of 2 to 7 carbon atoms, inclusive), in any combination, provided that no more than one acyl group may be present in any one compound; and wherein $R^8$ is lower alkyl or $-(CH_2)_nOR^{10}$ (wherein $R^{10}$ is hydrogen or alkanoyl of 2 to 7 carbon atoms, inclusive).

The most preferred embodiments of this invention include compounds of the following general structure, Formula XXI

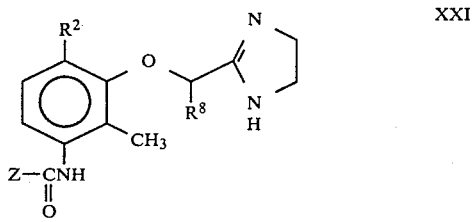

XXI

More specifically, the most preferred embodiments include compounds of Formula XXI wherein Z is alkyl of 1 to 6 carbon atoms, inclusive, or alkoxy of 1 to 6 carbon atoms, inclusive; wherein $R^2$ is hydrogen or methyl; and wherein $R^8$ is lower alkyl or $-(CH_2)_nOR^{10}$ (wherein $R^{10}$ is hydrogen or alkanoyl of 2 to 7 carbon atoms, inclusive).

The antidiarrheal activity of the compounds of this invention illustrated in the examples was tested by the following methods.

CHOLERA-INDUCED INTESTINAL FLUID SECRETION

Excessive fluid secretion into the intestinal lumen is a major component of diarrhea. In order to determine the effect of the test compounds on intestinal fluid movements, the rat cholera model was used. Female Charles River rats weighing 85–100 g and having free access to water were fasted for 24 hours prior to each experiment. After a midline incision was made under ether anesthesia, a 20-cm ligated small intestinal segment was constructed starting 3.0 cm distal to the ligament of Treitz. Each segment was injected, using a 27 gauge ½-inch needle, with 1.0 ml of a 40 mg/ml solution of crude cholera toxin (Wyeth) in a 0.9% saline solution. Thirty minutes before cholera toxin was injected, test compounds were administered subcutaneously to groups of four rats at doses of 10 and 20 mg/kg. Four hours after injection of toxin, the animals were sacrificed and the fluid content and exact length of the intestinal segments were measured. Fluid secretion was expressed in ml/cm of intestine.

The $ID_{50}$'s of these compounds were estimated from data obtained at least two doses and from at least two experiments using the method of maximum likelihood. Lower and upper limit values for the $ID_{50}$ between which the likelihood was more than one-twentieth of its maximum were used to define an interval of estimation, approximating a 95% confidence interval. The routine calculation did not include a test of the slope of the dose-response curve.

CASTOR-OIL-INDUCED DIARRHEA IN RATS

Employing the method of Niemegeers et al., castor-oil-induced diarrhea in rats was used to determine the antidiarrheal activity of test compounds with choleratoxin $ID_{50}$'s (see above) less than 10 mg/kg. Briefly, adult Charles River rats weighing 180-200 g and having free access to water were fasted for 24 hours prior to each experiment. Test compounds in 0.5% methylcellulose were administered intragastrically one hour before intragastric administration of 1.0 ml of castor oil per rat. Rats were observed for eight hours at hourly intervals after castor oil administration for the presence or absence of diarrhea. At each hourly interval $ED_{50}$'s were calculated for each compound using the method of Berkson.

See e.g., (1) H. J. Binder. "Net Fluid and Electrolyte Secretion: The Pathophysiologic Basis for Diarrhea." In *Mechanisms of Intestinal Secretion.* H. J. Binder, Ed. Alan R. Liss: New York, 1979; pp. 1–16; (2) H. I. Jacoby and C. H. Marshall. Antagonism of Cholera Enterotoxin by Anti-inflammatory Agents in the Rat. *Nature,* 235, 163–165 (1972); (3) R. A. Fischer. "Principles of Statistical Estimation." In *Statistical Methods for Research Workers,* 14th ed. Hafner: New York; pp. 301–339; (4) C. J. Niegemeers, F. M. Lennerts, and P. A. Janssen. Diphenoxin, the Active Metabolite of Diphenoxylate. *Arzneim.-Forsch.,* 22, 516–518 (1972); and (5) J. Berkson. A Statistically Precise and Relatively Simple Method of Estimating the Bioassay with Quantal Response Based on Logistic Function. *J. Am. Stat. Assn.,* 48, 565–599 (1953).

The compounds of this invention also exhibited analgesic activity in mice, as indicated by writhing and hotplate assays. The analgesic activity of the compounds of this invention illustrated in the examples was tested by the following methods.

HOT-PLATE ASSAY

Males Charles River mice (COBS CD-1(ICR)BR) weighing 20 to 30 grams were used in this assay. Two groups of 14 mice, brought into the experiment room approximately one-half hour before testing, were placed individually in a restraining cylinder placed on a hot plate kept at 55° (±0.5°) with a proportional temperature controller. The reaction time for each mouse to lick a foot or jump was measured three times at 20 minute intervals. Mice not responding within 15 seconds were discarded. Twenty minutes after the last reaction experiment ten mice were given a dose of the test compound and ten were given 0.9% saline (each containing approximately 0.09 ml of a 1:1 mixture by volume of propylene glycol and polysorbate 80) subcutaneously. The response times of the animals were measured as before at 30, 60, 90, and 120 minute intervals after this injection. Mice not responding with 30 seconds were removed from the hot plate and given a response time of 30 seconds. Analgesia is considered to be demonstrated in a mouse if the post-drug reaction time is greater than twice the median of the three pre-drug reaction times. A dose of a test compound was considered active if 50% of the animals showed analgesia. The $ED_{50}$ of each test compound was then calculated. See N. B. Eddy et al. *Synthetic Analgesics,* National Institute of Arthritis and Metabolic Diseases, National Institutes of Health, Bethesda, Md., pp. 385–393 (1952).

PBQ—Writhing Assay

Males Charles River albino mice (CD-1/HAM/ICR) weighing 20 to 30 grams were used in this assay. Thirty minutes after subcutaneous or intragastric administration of the test compound (0.1 ml per 10 g of body weight), a 0.025% solution of phenylbenzoquinone (PBQ) was injected intraperitoneally (0.1 ml per 10 g of body weight). Five minutes later each mouse was placed in a glass beaker and the number of writhes occurring in the next ten minutes was counted. (A writhe consists of dorsoflexion of the back, extension of the hindlimbs, and strong contraction of the abdominal musculature.) The test compound was considered to have produced analgesia in a mouse if the number of writhes elicited by PBQ was equal to or less than 50% of the median number of writhes recorded for the control group of mice that day. Results were expressed as the number of mice out of a possible ten in which the test compound produced analgesia. If the initial screening dose of 10 mg/kg inhibited writhing in greater than six of ten mice, the effect of additional doses of the compound on the writhing response was evaluated and an $ED_{50}$ was calculated.

By virtue of the antidiarrheal activity, the compounds of Formula I are useful in treating diarrhea in mammals. A physician or veterinarian of ordinary skill could readily determine whether a subject exhibits diarrhea. Moreover, by virtue of the analgesic activity, the compounds of Formula I are also useful in treating pain in mammals. A physician or veterinarian of ordinary skill could readily determine whether a subject requires relief from pain. The preferred utility relates to treatment of diarrhea. Regardless of the route of administration selected, the compounds of the present invention are formulated into pharmaceutically acceptable dosage forms by conventional methods known to those skilled in the art. The compounds may be formulated using pharmacologically acceptable acid addition salts. Moreover, the compounds or their salts may be used in a suitable hydrated form.

The compounds can be administered in such oral dosage forms as tablets, capsules, pills, powders, or granules. They may also be administered intraperitoneally, subcutaneously, or intramuscularly, using forms known to the pharmaceutical art. In general, the preferred form of administration is oral. An effective but non-toxic quantity of the compound is employed in treatment. The dosage regimen for preventing or treating diarrhea or pain by the compounds of this invention is selected in accordance with a variety of factors, including the type, age, weight, sex, and medical condition of the patient; the severity of the diarrhea or pain; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention are ordinarily in the range of 0.01 to 1.0 mg/kg up to about 100 mg/kg orally when used as antidiarrheal agents.

The following examples further illustrate details for the preparation of the compounds of this invention. The invention, which is set forth in the foregoing disclosure, is not be construed or limited either in spirit or in scope by these examples. Those skilled in the art will readily understand that known variations of the conditions and processes of the following preparative procedures can be used to prepare these compounds. All temperatures are degrees celsius unless otherwise noted.

DESCRIPTION OF THE PREFERRED EMBODIMENTS

EXAMPLE 1 ethyl 2-(2-methyl-3-nitrophenoxy)butanoate

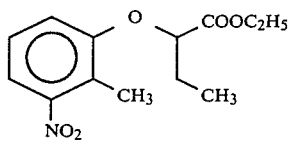

A mixture of 5.0 g (32 mmole) of 2-methyl-3-nitrophenol, 4.8 ml (ca. 32 mmole) of ethyl 2-bromobutanoate, and 4.5 g (32 mmole) of potassium carbonate in 50 ml of dimethylformamide was stirred for 18 hours at room temperature. The mixture was then poured over ice, diluted with water, and extracted twice with diethyl ether. The combined organic extract was washed with water, dried over magnesium sulfate, filtered, and concentrated in vacuo to give 8.0 g of the title compound as an analytically pure solid. Structure assignment was supported by nmr and infrared spectra and by elemental analysis.

nmr (CDCl$_3$): δ(ppm) 1.0–1.4 (m's, 6H, ethyl and propylidene CH$_3$'s); 1.85–2.35 (m, 2H, propylidene CH$_2$); 2.45 (s, 3H, phenyl CH$_3$); 4.25 (q, 2H, ethyl CH$_2$); 4.68 (t, 1H, propylidene CH); 6.8–7.6 (m, 3H, phenyl CH's)

IR (KBr): 1750 cm$^{-1}$

Analysis. Calcd. for C$_{13}$H$_{17}$NO$_5$: C, 58.42; H, 6.41; N, 5.24. Found: C, 58.44; H, 6.41; N, 5.27.

EXAMPLE 2

4,5-dihydro-2-[1-(2-methyl-3-nitrophenoxy)propyl]-1H-imidazole

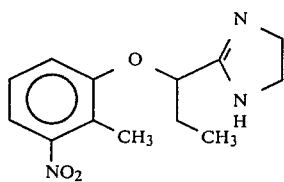

A solution of 2.0N trimethylaluminum (20.5 ml, 41 mmole) in toluene was diluted with 20 ml of toluene and cooled to −20°. Ethylenediamine (2.8 ml, ca. 41 mmole) was then added slowly as the temperature was maintained below +10°. After recooling the mixture to about 0°, the title product of Example 1 (dissolved in 10 ml of toluene) was added, and the resultant mixture was heated at reflux for four hours. The mixture was allowed to cool to room temperature and the reaction was quenched by adding 2.0 ml of water. After adding 20 ml each of dichloromethane and methanol and stirring for about fifteen minutes, a solid was collected and chromatographed on silica gel using methanol-dichloromethane-ammonium hydroxide as eluent. The title compound was isolated as 2.3 g of a nearly pure solid. Structure assignment was supported by nmr and infrared spectra.

nmr (CDCl$_3$): δ(ppm) 1.1 (t, 3H, propylidene CH$_3$); 2.0 (m, 2H, propylidene CH$_2$); 2.4 (s, 3H, phenyl CH$_3$); 3.4 (m, 4H, imidazoline CH$_2$'s); 4.8 (dd, 1H, propylidene CH); 7.0–7.5 (m, 3H, phenyl CH's)

IR(KBr): 1611 cm$^{-1}$

EXAMPLE 3

3-[1-(4,5-dihydro-1H-imidazol-2-yl)]propoxy-2-methyl-benzenamine dihydrochloride hemihydrate (SC-39980)

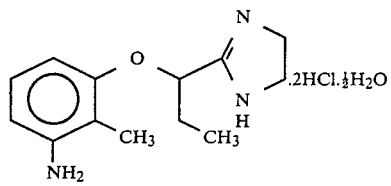

A solution of 2.3 g (8.8 mmole) of the title product of Example 2 in ethanol containing hydrochloric acid was hydrogenated using 10% palladium on carbon as catalyst. After insolubles were removed by filtration and the filtrate concentrated in vacuo, the resultant solid was suspended in 5% methanol-acetone. Filtration, followed by an acetone wash, afforded 5.4 g of the title compound as an analytically pure solid. Structure assignment was supported by nmr and infrared spectra and by elemental analysis.

nmr (CDCl$_3$): δ(ppm) 1.0 (t, 3H, propylidene CH$_3$); 2.1 (m, 2H, propylidene CH$_2$); 2.25 (s, 3H, phenyl CH$_3$); 3.8 (m, 4H, imidazoline CH$_2$'s); 5.3 (t, 1H, propylidene CH); 6.8–7.2 (m, 3H, phenyl CH's)

IR(KBr): 1615 cm$^{-1}$

Analysis. Calcd. for C$_{13}$H$_{19}$N$_3$O.2HCl.½H$_2$O: C, 49.52; H, 7.03: N, 13.33. Found: C, 49.77; H, 6.96; N, 13.54.

EXAMPLE 4

3-[1-(4,5-dihydro-1H-imidazol-2-yl)]ethoxy-2-methyl-benzenamine dihydrochloride monohydrate (SC-37230)

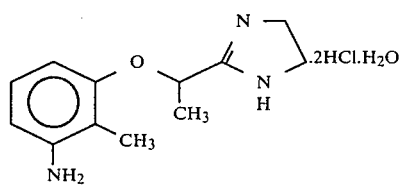

The title compound (5.4 g) was prepared by the methods of Examples 1, 2, and 3 using ethyl 2-bromopropanoate instead of ethyl 2-bromobutanoate. Structure assignment was supported by nmr and infrared spectra and by elemental analysis.

nmr (CD$_3$$_2$SO): δ(ppm) 1.6 (d, 3H, ethylidene CH$_3$); 2.3 (s, 3H, phenyl CH$_3$); 3.8 (m, 4H, imidazoline CH$_2$'s); 5.5 (q, 1H, ethylidene CH); 6.9–7.5 (m, 3H, phenyl CH's)

IR(KBr): 1595, 1614 cm$^{-1}$

Analysis. Calcd. for C$_{12}$H$_{17}$N$_3$O.2HCl.H$_2$O: C, 46.46; H, 6.82: N, 13.54; Cl, 22.85. Found: C, 46.78; H, 6.52; N, 13.69; Cl, 23.00.

EXAMPLE 5 ethyl 2-(4-bromo-2,6-dimethyl-3-nitrophenoxy)propanoate

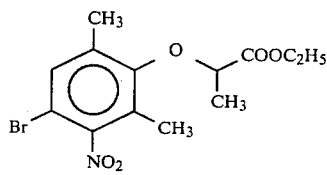

Ethyl 2-(4-bromo-2,6-dimethylphenoxy)propanoate (92.8 g, 307 mmole), prepared by the method of Example 1 from 4-bromo-2,6-dimethylphenol, was dissolved in 320 ml of cold (−10°) concentrated sulfuric acid. While maintaining the temperature below 0°, 22.4 ml of 70% nitric acid was added slowly. After fifteen minutes the reaction mixture was poured onto ice and diluted to 1.0 l with water, then extracted with two portions of diethyl ether. The organic portion was washed repeatedly with aqueous sodium bicarbonate and then with water. The organic layer was dried over magnesium sulfate, filtered, and concentrated in vacuo to dryness. Chromatography on silica gel (ethyl acetate-hexane eluent) afforded the title compound. Structure assignment was supported by nmr and infrared spectra.

nmr (CDCl$_3$): δ(ppm) 1.25 (t, 3H, ethyl CH$_3$); 1.6 (d, 3H, ethylidene CH$_3$); 2.25 & 2.35 (pair s's, 6H, phenyl CH$_3$'s); 4.2 (q, 2H, ethyl CH$_2$); 4.55 (q, 1H, ethylidene CH); 7.33 (s, 1H, phenyl 5-CH)

IR(KBr): 1740 cm$^{-1}$

EXAMPLE 6

4,5-dihydro-2-[1-(4-bromo-2,6-dimethyl-3-nitrophenoxy)propyl]-1H-imidazole

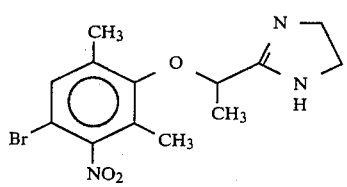

The title compound (24.8 g) was prepared by the method of Example 2 using 31.1 g (87 mmole) of the title product of Example 5. Structure assignment was supported by nmr and infrared spectra.

nmr (CD$_3$): δ(ppm) 1.45 (d, 3H, ethylidene CH$_3$); 2.16 & 2.3 (pair s's, 6H, phenyl CH$_3$'s); 3.43 (s, 4H, imidazoline CH$_2$'s); 4.6 (q, 1H, ethylidene CH); 7.6 (s, 1H, phenyl 5-CH)

IR(KBr): 1605 cm$^{-1}$

EXAMPLE 7

3-[1-(4,5-dihydro-1H-imidazol-2-yl)ethoxy]-2,4-dimethylbenzenamine hydrobromide ¼ hydrate (SC-39674)

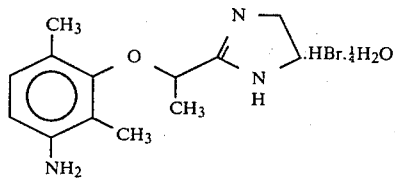

The title product of Example 6 (14.8 g) was hydrogenated in ethanol using 10% palladium on carbon as catalyst. Insolubles were removed by filtration and the filtrate was concentrated to an oil which solidified upon standing. The solid was triturated with diethyl ether and collected by filtration, giving the debrominated title compound (11.2 g) as a hydrated hydrobromide salt. Structure assignment was supported by nmr and infrared spectra and by elemental analysis.

nmr ((CD$_3$)$_2$SO): δ(ppm) 1.5 (d, 3H, ethylidene CH$_3$); 2.0 & 2.1 (pair s's, 6H, phenyl CH$_3$'s); 3.9 (s, 4H, imidazoline CH$_2$'s); 4.9 (q, 1H, ethylidene CH); 6.45 & 6.8 (pair d's, 2H, phenyl CH's)

IR(KBr): 1598, 1612 cm$^{-1}$

Analysis. Calcd. for C$_{13}$H$_{19}$N$_3$O.HBr.¼H$_2$O: C, 48.98; H, 6.48: N, 13.18; Br, 25.06. Found: C, 49.08; H, 6.40; N, 13.21; Br, 24.71.

EXAMPLE 8

3-[1-(4,5-dihydro-1H-imidazol-2-yl)ethoxy]-6-bromo-2,4-dimethylbenzenamine (SC-40135)

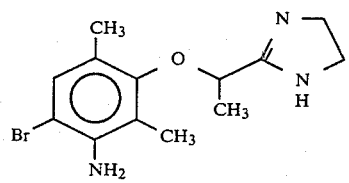

The title compound (539 mg) was prepared from the title product of Example 5 using the general hydrogenation method of Example 7, except that platinum was used as catalyst and purification was effected by column chromatography on silica gel (methanol-dichloromethaneammonium hydroxide eluent). No debrominated byproduct (see Example 7) was isolated. Structure assignment was supported by nmr and infrared spectra and by elemental analysis.

nmr ((CD$_3$)$_2$SO): δ(ppm) 1.36 (d, 3H, ethylidene CH$_3$); 2.05 & 2.09 (pair s's, 6H, phenyl CH's); 3.43 (s, 4H, imidazoline CH$_2$'s); 4.39 (q, 1H, ethylidene CH)

IR(KBr): 1623 cm$^{-1}$

Analysis. Calcd. for C$_{13}$H$_{18}$N$_3$OBr: C, 50.01; H, 5.81; N, 13.46; Br, 25.59. Found: C, 49.91; H, 5.95; N, 13.47; Br, 25.71.

EXAMPLE 9

3-(2-methyl-3-nitrophenoxy)oxacyclopentan-2-one

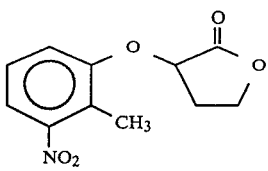

The title compound was prepared by the method of Example 1 using 2-bromo-4-hydroxybutanoic lactone instead of ethyl 2-bromobutanoate. (Additional portions of the lactone were required to bring the reaction to completion.) Chromatography on silica gel, using ethyl acetate-hexane as eluent, afforded 9.0 g of the title compound as an analytically pure solid. Structure assignment was supported by nmr and infrared spectra and by elemental analysis.

nmr ((CD$_3$)$_2$SO): δ(ppm) 2.6 (s, 3H, phenyl CH$_3$); 2.5–3.0 (m, 2H, lactone CH$_2$); 4.1–4.6 (m, 2H, lactone OCH$_2$); 5.4 (dd, 1H, lactone CH); 7.4 (m, 3H, phenyl CH's);

IR(KBr): 1778 cm$^{-1}$

Analysis. Calcd. for C$_{11}$H$_{11}$NO$_5$: C, 55.70; H, 4.67; N, 5.90. Found: C, 55.53; H, 4.80; N, 5.80.

EXAMPLE 10

4,5-dihydro-2-[1-(2-methyl-3-nitrophenoxy)-3-hydroxypropyl]-1H-imidazole

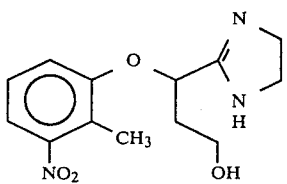

The title compound (1.3 g) was prepared by the method of Example 2 using the title product of Example 9. Structure assignment was supported by nmr and infrared spectra and by elemental analysis.

nmr ((CD$_3$)$_2$SO): δ(ppm) 2.1 (m, 2H, hydroxyethylidene CH$_2$); 2.3 (s, 3H, phenyl CH$_3$); 3.4 (s, 4H, imidazoline CH$_2$'s); 3.6 (t, 2H, hydroxyethylidene OCH$_2$); 5.0 (t, 1H, hydroxyethylidene CH); 7.1–7.5 (m, 3H, phenyl CH's)

IR(KBr): 1621 cm$^{-1}$

Analysis. Calcd. for C$_{13}$H$_{17}$N$_3$O$_4$: C, 55.91; H, 6.13; N, 15.05. Found: C, 55.44; H, 5.91; N, 14.73.

EXAMPLE 11

3-[1-(4,5-dihydro-1H-imidazol-2-yl)-3-hydroxypropoxy]-2-methylbenzenamine dihydrochloride ¼ hydrate (SC-40463)

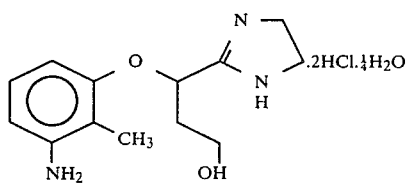

The title compound was prepared by the method of Example 3 using the title product of Example 10. Structure assignment was supported by nmr spectrum and by elemental analysis.

nmr ((CD$_3$)$_2$SO): δ(ppm) 2.0–2.5 (m, 5H, propylidene CH$_2$ and phenyl CH$_3$); 3.6 (t, 2H, hydroxyethylidene OCH$_2$); 3.8 (s, 4H, imidazoline CH$_2$'s); 5.4 (t, 1H, hydroxyethylidene CH); 6.8–7.5 (m, 3H, phenyl CH's)

Analysis. Calcd. for C$_{13}$H$_{19}$N$_3$O$_2$·2HCl·¼H$_2$O: C, 47.78; H, 6.63; N, 12.87; Cl, 21.70. Found: C, 47.52; H, 6.55; N, 12.63; Cl, 21.76.

EXAMPLE 12 ethyl 2-(2-bromo-4,6-dimethyl-3-nitrophenoxy)propanoate

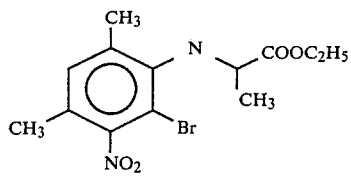

To a solution of 24 g (0.2 mole) of 2,4-dimethylphenol in 500 ml of tetrahydrofuran was added 80 g (0.2 mole) of pyridimium bromide perbromide. After one hour the reaction mixture was shaken with water and diethyl ether. The organic layer was separated and washed with water and then with aqueous sodium bicarbonate until the aqueous extract remained alkaline. The organic phase was dried over magnesium sulfate, filtered, and concentrated in vacuo to an oil (61.5 g). A portion of the 2-bromo-4,6-dimethylphenol thus formed was used without further purification to prepare the title compound by the methods of Examples 1 and 5. (Following the nitration reaction, by the method of Example 5, the 3-nitro product was separated from 5-nitro and other byproducts during chromatography.) The title compound (2.7 g) was used in subsequent reactions without further purification.

EXAMPLE 13

4,5-dihydro-2-[1-(2-bromo-4,6-dimethyl-3-nitrophenoxy)propyl]-1H-imidazole

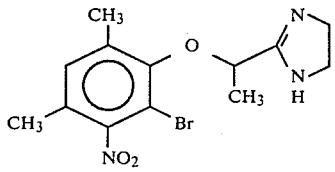

The title compound was prepared by the method of Example 2 using 2.7 g (7.8 mmole) of the title product of Example 12, except that chromatography was not needed to afford a pure crystalline solid (1.2 g). Structure assignment was supported by elemental analysis.

Analysis. Calcd. for C$_{13}$H$_{16}$N$_3$O$_3$Br: C, 45.63; H, 4.71; N, 12.28; Br, 23.35. Found: C, 45.30; H, 4.74; N, 12.43; Br, 23.16.

EXAMPLE 14

3-[1-(4,5-dihydro-1H-imidazol-2-yl)ethoxy]-4,6-dimethylbenzenamine hydrobromide "solvate" (SC-40702)

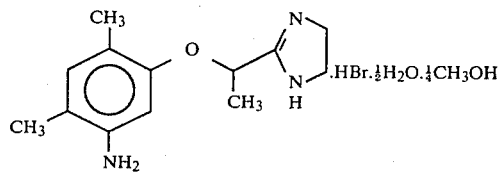

The title compound was prepared by the method of Example 7 using title product of Example 13. The title compound was isolated as the hydrobromide salt partially solvated with water and methanol. Structure assignment was supported by elemental analysis.

Analysis. Calcd. for $C_{13}H_{19}N_3O\cdot HBr\cdot\frac{1}{2}H_2O\cdot\frac{1}{4}C_{H_3}OH$: C, 48.61; H, 6.55; N, 12.70; Br, 24.16. Found: C, 48.25; H, 6.26; N, 12.54; Br, 24.44.

EXAMPLE 15 ethyl N-[3-[1-(4,5-dihydro-1H-imidazol-2-yl)ethoxy]-2,4-dimethylphenyl]carbamate hemihydrate (SC-40020)

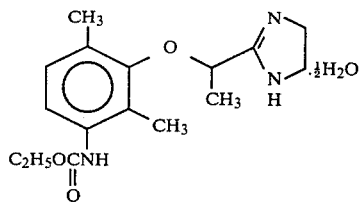

To a stirred suspension of the title product of Example 7 (5.0 g, 15.9 mmole) in 130 ml of acetonitrile was added 13.8 ml (ca. 16 mmole) of 12% phosgene in toluene. After 18 hours 25 ml absolute ethanol was added, and the mixture was stirred for one hour. Volatiles were removed in vacuo and the residue was dissolved in water. After adjusting to pH 10 with dilute sodium hydroxide, the solution was extracted with two portions of diethyl ether, and the combined organic layers were washed with water, dried over magnesium sulfate, filtered, and concentrated in vacuo. The solid that crystallized during the concentration was triturated with diethyl ether and collected by filtration to give 2.2 g of the title compound as the hemihydrate. Structure assignment was supported by nmr and infrared spectra and by elemental analysis.

nmr (CDCl$_3$): δ(ppm) 1.1–1.5 (t & d, 6H, ethyl and ethylidene CH$_3$'s); 2.15 & 2.25 (pair s's, 6H, phenyl CH$_3$'s); 3.6 (s, 4H, imidazoline CH$_2$'s); 4.2 (q, 2H, ethyl CH$_2$); 4.6 (q, 1H, ethylidene CH); 6.9 & 7.6 (pair d's, 2H, phenyl CH's)

IR(KBr): 1706 cm$^{-1}$

Analysis. Calcd. for $C_{16}H_{23}N_3O_3\cdot\frac{1}{2}H_2O$: C, 61.12; H, 7.69; N, 13.36. Found: C, 61.06; H, 7.41; N, 13.29.

EXAMPLE 16 ethyl N-[3-[1-(4,5-dihydro-1H-imidazol-2-yl)ethoxy]-2-methylphenyl]carbamate hydrate (SC-39110)

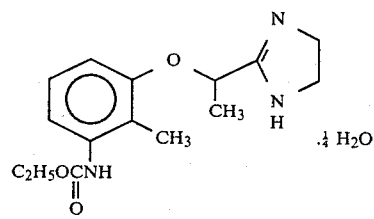

The title compound (3.4 g) was prepared by the method of Example 15 using title product of Example 4. Structure assignment was supported by nmr and infrared spectra and by elemental analysis.

nmr ((CD$_3$)$_2$SO): δ(ppm) 1.2 (t, 3H, ethyl CH$_3$); 1.5 (d, 3H, ethylidene CH$_3$); 2.1 (s, 3H, phenyl CH$_3$); 3.45 (s, 4H, imidazoline CH$_2$'s); 4.1 (q, 2H, ethyl CH$_2$); 4.9 (q, 1H, ethylidene CH); 6.7–7.2 (pair d's, 3H, phenyl CH's)

IR(KBr): 1710, 1731 cm$^{-1}$

Analysis. Calcd. for $C_{15}H_{21}N_3O_3\cdot\frac{1}{4}H_2O$: C, 60.89; H, 7.32; N, 14.20. Found: C, 60.93; H, 7.21; N, 14.25.

EXAMPLE 17

N-[3-[1-(4,5-dihydro-1H-imidazol-2-yl)ethoxy]-2-methylphenyl]acetamide hemihydrate (SC-37860)

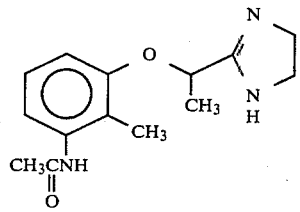

The title compound of Example 4 (1.5 g, 4.8 mmole) was stirred in 60 ml of acetonitrile containing 2.3 ml (ca. 24 mmole) of acetic anhydride. After 18 hours the reaction mixture was concentrated to dryness in vacuo and the residue was dissolved in water. The solution was then made alkaline with aqueous sodium bicarbonate and extracted with dichloromethane. After the organic phase was dried over magnesium sulfate, filtered, and concentrated in vacuo, the residue was recrystallized from diethyl ether to give 398 mg of the title compound. Structure assignment was supported by nmr spectrum and by elemental analysis.

nmr ((CD$_3$)$_2$SO): δ(ppm) 1.4 (d, 3H, ethylidene CH$_3$); 2.01 & 2.03 (pair s's, 6H, acetyl and phenyl CH$_3$'s); 3.3 (s, 4H, imidazoline CH$_2$'s); 4.8 (q, 1H, ethylidene CH); 6.5–7.2 (pair d's, 3H, phenyl CH's)

Analysis. Calcd. for $C_{14}H_{19}N_3O_2\cdot\frac{1}{2}H_2O$: C, 62.20; H, 7.45; N, 15.54. Found: C, 62.57; H, 7.25; N, 15.14.

EXAMPLE 18 methyl 2-(2-methyl-3-aminophenoxy)propanoate

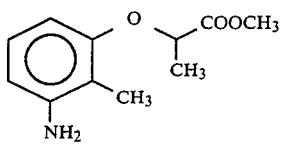

Methyl 2-(2-methyl-3-nitrophenoxy)propanoate (8.2 g, 40 mmole), prepared by the method of Example 1 using methyl 2-bromopropanoate, was hydrogenated in 250 ml of ethanol using 1.0 g of Raney nickel. After reduction was complete, insolubles were removed by filtration and the filtrate concentrated in vacuo. The resultant solid (7.7 g) was used in further reactions without further characterization.

EXAMPLE 19 methyl 2-[2-methyl-3-(dimethylamino)phenoxy]propanoate

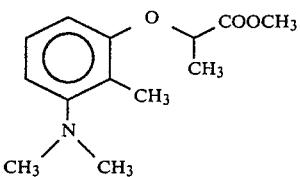

To a mixture of 7.7 g (ca. 37 mmole) of the title product of Example 18, 2.1 ml of acetic acid, 30 ml of 37% formaldehyde, and 50 ml of acetonitrile was added 2.3 g (37 mmole) of sodium cyanoborohydride. After the amino compound had been consumed, aqueous sodium hydroxide was added and the mixture extracted with diethyl ether. The organic phase was washed with water, dried over magnesium sulfate, filtered, and concentrated in vacuo. The residue was chromatographed on silica gel using ethyl acetate-hexane as eluent, giving the title compound (4.2 g) as an oil. The compound was used in subsequent reeactions without further purification.

EXAMPLE 20

N,N-dimethyl-3-[1-(4,5-dihydro-1H-imidazol-2-yl)ethoxy]-2-methylbenzenamine (SC-37454)

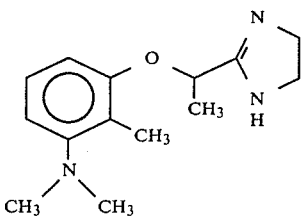

The title compound (1.5 g) was prepared by the method of Example 2 using the title product of Example 19. Structure assignment was supported by nmr and infrared spectra and by elemental analysis.

nmr ((CDCl$_3$): δ(ppm) 1.6 (d, 3H, ethylidene CH$_3$); 2.22 (s, 3H, phenyl CH$_3$); 2.66 (s, 6H, amino CH$_3$'s); 3.6 (m, 4H, imidazoline CH$_2$'s); 5.0 (q, 1H, ethylidene CH); 6.5–7.3 (m, 3H, phenyl CH's)

IR (KBr): 1608 cm$^{-1}$

Analysis. Calcd. for C$_{14}$H$_{21}$N$_3$O: C, 67.99; H, 8.56; N, 16.99. Found: C, 67.67; H, 8.69; N, 16.66.

EXAMPLE 21

3-[1-(1-methyl-4,5-dihydro-1H-imidazol-2-yl)ethoxy]-2-methylbenzenamine hydrochloride

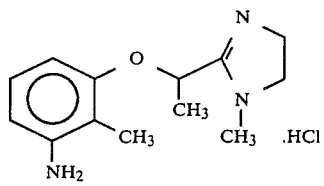

A mixture of p-toluenesulfonic acid, dried by azeotroping the hydrate (0.1 mole) with benzene, N-methylethylenediamine (0.1 mole), and ethyl 2-(2-methyl-3-nitrophenoxy)propanoate (0.05 mole, prepared by the method of Example 1 using 2-methyl-3-nitrophenol) is heated to 240° to remove volatiles. After one hour at 230° the mixture is allowed to cool and then partitioned between 5% aqueous sodium hydroxide and diethyl ether. The organic layer is washed with two portions of water, dried over magnesium sulfate, concentrated to dryness, and purified by column chromatography on silica gel. The intermediate nitro compound is then converted to the title compound by the method of Example 3.

What is claimed is:

1. A compound of the formula:

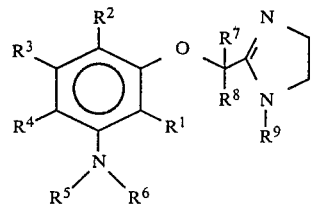

wherein $R^1$ and $R^3$, each being the same or different, are:
  (a) hydrogen; or
  (b) alkyl or 1 to 6 carbon atoms, inclusive;
wherein $R^2$ and $R^4$, each being the same or different, are:
  (a) hydrogen; or
  (b) alkyl of 1 to 6 carbon atoms, inclusive; with the proviso that $R^1$ and $R^2$ may not both be hydrogen;
wherein $R^5$ is hydrogen;
wherein $R^6$ is:
  (a) alkanoyl of 2 to 7 carbon atoms, inclusive; or
  (b) alkoxycarbonyl of 2 to 7 carbon atoms, inclusive;
wherein $R^7$ is:
  (a) hydrogen; or
  (b) alkyl of 1 to 6 carbon atoms, inclusive;
wherein $R^8$ is alkyl of 1 to 6 carbon atoms, inclusive;
wherein $R^9$ is:
  (a) hydrogen; or
  (b) alkyl of 1 to 6 carbon atoms, inclusive;
or a pharmacologically acceptable salt; the compound being either hydrated or unhydrated.

2. A compound according to claim 1 having the formula:

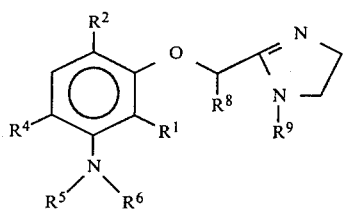

3. A compound according to claim 2 wherein $R^9$ is hydrogen.

4. A compound according to claim 3 wherein $R^1$ is alkyl of 1 to 6 carbon atoms, inclusive.

5. A compound according to claim 4 having the formula:

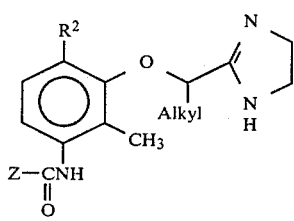

wherein Z is:
(a) alkyl of 1 to 6 carbon atoms, inclusive; or
(b) alkoxy of 1 to 6 carbon atoms, inclusive;

6. A compound according to claim 5 wherein Z is alkoxy of 1 to 6 carbon atoms, inclusive.

7. ethyl N-[3-[1-(4,5-dihydro-1H-imidazol-2-yl)ethoxy]-2-methylphenyl]carbamate, a compound according to claim 6.

8. ethyl N-[3-[1-(4,5-dihydro-1H-imidazol-2-yl)ethoxy]-2,4-dimethylphenyl]carbamate, a compound according to claim 6.

9. A compound according to claim 5 wherein Z is alkyl of 1 to 6 carbon atoms, inclusive.

10. N-[3-[1-(4,5-dihydro-1H-imidazol-2-yl)ethoxy]-2-methylphenyl]acetamide, a compound according to claim 9.

11. A compound of the formula:

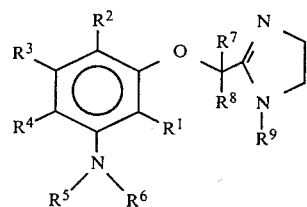

wherein $R^1$ and $R^3$, each being the same or different, are:
(a) hydrogen; or
(b) alkyl of 1 to 6 carbon atoms, inclusive;
wherein $R^2$ and $R^4$, each being the same or different, are:
(a) hydrogen; or
(b) alkyl of 1 to 6 carbon atoms, inclusive; with the proviso that $R^1$ and $R^2$ may not both be hydrogen;
wherein $R^5$ is:
(a) hydrogen; or
(b) alkyl of 1 to 6 carbon atoms, inclusive;
wherein $R^6$ is:
(a) hydrogen;
(b) alkyl of 1 to 6 carbon atoms, inclusive,
(c) alkanoyl of 2 to 7 carbon atoms, inclusive; or
(d) alkoxycarbonyl of 2 to 7 carbon atoms, inclusive;
wherein $R^7$ is:
(a) hydrogen; or
(b) alkyl of 1 to 6 carbon atoms, inclusive;
wherein $R^8$ is $(CH_2)_nOR^{10}$;
wherein $R^9$ is:
(a) hydrogen; or
(b) alkyl of 1 to 6 carbon atoms, inclusive;
wherein $R^{10}$ is:
(a) hydrogen; or
(b) alkanoyl of 2 to 7 carbon atoms, inclusive;
wherein n is an integer of 1 to 6, inclusive; or a pharmacologically acceptable salt; the compound being either hydrated or unhydrated.

12. A compound according to claim 11 having the formula:

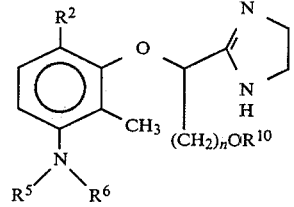

13. 3-[1-(4,5-dihydro-1H-imidazol-2-yl)-3-hydroxypropoxy]-2-methylbenzenamine, a compound according to claim 12.

* * * * *